United States Patent
Akura et al.

(10) Patent No.: US 12,349,888 B2
(45) Date of Patent: Jul. 8, 2025

(54) PUPIL EXPANSION DEVICE

(71) Applicant: MIRAI EYE INC., Hyogo (JP)

(72) Inventors: Junsuke Akura, Hyogo (JP); Zenku Haga, Fukuoka (JP)

(73) Assignee: Mirai Eye Inc., Hyogo (JP)

(*) Notice: Subject to any disclaimer, the term of this patent is extended or adjusted under 35 U.S.C. 154(b) by 239 days.

(21) Appl. No.: 17/926,766

(22) PCT Filed: Jun. 24, 2021

(86) PCT No.: PCT/JP2021/023926
§ 371 (c)(1),
(2) Date: Nov. 21, 2022

(87) PCT Pub. No.: WO2021/261551
PCT Pub. Date: Dec. 30, 2021

(65) Prior Publication Data
US 2023/0200794 A1    Jun. 29, 2023

(30) Foreign Application Priority Data

Jun. 26, 2020 (JP) ................................. 2020-110534

(51) Int. Cl.
*A61B 17/02* (2006.01)
*A61F 9/007* (2006.01)

(52) U.S. Cl.
CPC ...... *A61B 17/0231* (2013.01); *A61B 17/0293* (2013.01); *A61F 9/007* (2013.01)

(58) Field of Classification Search
CPC ............ A61B 17/0231; A61B 17/0293; A61B 2017/0225; A61F 9/007
See application file for complete search history.

(56) References Cited

U.S. PATENT DOCUMENTS

| 6,068,643 | A | * | 5/2000 | Milverton ......... A61B 17/0231 |
| | | | | 606/107 |
| 10,433,828 | B2 | | 10/2019 | Cote et al. |
| 11,389,150 | B2 | | 7/2022 | Cote et al. |
| 2013/0096386 | A1 | | 4/2013 | Christensen et al. |

(Continued)

FOREIGN PATENT DOCUMENTS

| JP | 2014193248 A | 10/2014 |
| JP | 2016513576 A | 5/2016 |

OTHER PUBLICATIONS

International Search report PCT/JP2021/023926 dated Aug. 31, 2021 (pp. 1-2).

*Primary Examiner* — Julianna N Harvey
(74) *Attorney, Agent, or Firm* — Millen, White, Zelano & Branigan P.C.; William F. Nixon (57) ABSTRACT

The pupil expander is used to expand a pupil in ophthalmic surgery and includes a ring portion forming a ring and an iris hooking portion provided to the ring portion. The ring portion includes a first ring portion formed in a shape curved radially inward and a second ring portion formed in a shape curved radially outward, the first ring portion and the second ring portion being arranged alternately along a circumferential direction of the ring portion. The first ring portion is provided with the iris hooking portion. The iris hooking portion is configured to be hooked on a pupillary margin of an iris in a manner such that the first ring portion and the second ring portion are arranged on a front surface side of the iris.

11 Claims, 9 Drawing Sheets

(56) References Cited

U.S. PATENT DOCUMENTS

| | | | |
|---|---|---|---|
| 2014/0378773 A1* | 12/2014 | Dykes | A61F 9/0017 |
| | | | 600/208 |
| 2016/0030239 A1* | 2/2016 | Akura | A61B 17/0231 |
| | | | 606/107 |
| 2016/0051244 A1* | 2/2016 | Akura | A61B 17/0206 |
| | | | 600/236 |
| 2016/0081685 A1* | 3/2016 | Dykes | A61F 9/0017 |
| | | | 606/107 |
| 2017/0265851 A1* | 9/2017 | Kahook | A61B 3/00 |

* cited by examiner

PUPIL EXPANSION DEVICE

TECHNICAL FIELD

The present invention relates to a pupil expander used to expand a pupil in ophthalmic surgery, such as, e.g., cataract surgery.

BACKGROUND ART

Normally, a human eye has a function of adjusting an amount of light incident from a pupil located at the center of an iris. An iris is formed of ring-shaped tissues and located behind a cornea and in front of a crystalline lens, the center of which opens to form a pupil. An iris is formed of expandable course connective tissues and muscles for expanding and contracting a pupil. In a bright place, the tissues of the iris develop afferently to shrink the pupil (miosis), thereby reducing the amount of light entering into the eye. In a dark place, the tissues of the iris shrinks toward its root (the peripheral portion of the pupil) to enlarge the pupil (mydriasis), thereby increasing the amount of light entering into the eye.

Note that diseases occurring in a human eye include a disease called a cataract in which a crystalline lens becomes cloudy mainly due to aging, causing vision deterioration. In current cataract surgery, the main stream is to apply phacoemulsification and intraocular lens implantation. In this surgery, a circular incision of about 5 mm to 6 mm is formed at the center of an anterior capsule in a lens capsule. Then, the turbid contents of the crystalline lens are aspirated through the incision to be removed, and an intraocular lens is inserted into the crystalline lens capsule via the incision.

In order to complete surgery of a crystalline lens, a vitreous body, or a retina in an eyeball, which is located behind the iris, such as, e.g., cataract surgery and vitreoretinal surgery described above, it is required to maintain the diameter of the pupil in a dilated (mydriatized) state of a sufficiently large size (about 5 mm to 8 mm) during the surgery. However, in a case of an eye previously inflamed in the iris, an eye with miotic instillation for a long time due to glaucoma, an eye with pseudo-exfoliative materials attached to the iris, or an eye with severe senile miosis, there is a case in which it is not possible to fully expand the pupil even if a mydriatic agent is applied before the surgery.

For an eye in which the pupil cannot be fully expanded as described above, conventionally, an iris retractor having a hook-like tip end portion has been used (e.g., see Patent Document 1 listed below). A case in which surgery using four iris retractors will be described below. When installing the iris retractors, four incisions are formed in the cornea, and the iris retractors are inserted through the respective incisions. Then, the tip ends of the iris retractors are hooked on the respective positions of the pupillary margin of the iris to pull the pupillary margin of the iris radially outward. In this state, each iris retractor is fixed to the cornea using a silicone stopper. With this, the diameter of the pupil is maintained in a state of being sufficiently expanded. When removing the iris retractor, the silicone stopper is loosed and then each retractor is removed. Such installation and removal of the iris retractor must be performed carefully to not cause damage to the iris, which requires considerable labor and time. In particular, in the iris retractor, a hook portion for hooking on a pupillary margin of an iris is formed of a thin resin wire. For this reason, there is a problem that the pupillary margin of the iris may be torn when the pupillary margin of the iris is pulled by the iris retractor, resulting in a deformation of the pupil after the surgery.

On the other hand, in recent years, a pupil expander, such as, e.g., Malyugin Ring, The OASIS Iris Expander, and Morcher Pupil Dilator, has been known as a pupil expander which is simpler than the above-described iris retractor and can expand a pupil in a short time (see, e.g., Patent Documents 2 to 4 listed below). These pupil expanders are made of plastic having a high-shape-memory properties and are formed in, in a natural state, a quadrangular shape or a substantially ring-shape with one portion opened. These pupil expanders are stored in a dedicated injector in a state of being folded into a long thin shape and inserted into an eye through a small incision of about 2.2 mm to 3.2 mm to be fitted to the pupillary margin of the iris. Then, the pupil is expanded radially outward by being hooked from the inner side of the pupillary margin of the iris by the iris hooking portions formed at 4 to 5 positions or substantially over the entire circumference.

PRIOR ART DOCUMENT

Patent Document

Patent Document 1: Japanese Unexamined Patent Application Publication No. H07(1995)-194643

Patent Document 2: Japanese Unexamined Patent Application Publication (Translation of PCT application) No. 2010-521229

Patent Document 3: Japanese Unexamined Patent Application Publication (Translation of PCT application) No. 2002-531170

Patent Document 4: Japanese Unexamined Patent Application Publication (Translation of PCT application) No. H09(1997)-505753

SUMMARY OF THE INVENTION

Problems to be Solved by the Invention

However, a conventional pupil expander is made of a material with high-shape-memory properties. Therefore, when released from an injector into an eye, the pupil expander returns to its original shape (natural shape) within the eye. Then, the pupil expander expands into a square shape or a circular shape having a diameter of about 6 mm to about 9 mm on the iris within the eye. For this reason, after hooking the iris hooking portion of the pupil expander on the pupillary margin using a medical instrument, such as, e.g., a Sinskey hook, when it is tried to hook the other iris hooking portion on its adjacent pupillary margin or the opposite pupillary margin with the other iris hooking portion, it is required to largely move the iris hooking portion eccentrically in a state in which it is opened widely. In view of this, the difficulty of the operation has not been sufficiently solved. Therefore, when installing a pupil expander, there is a possibility of causing damage to the iris tissues by contacting the cornea endothelium which is important for maintaining the transparency of the cornea or by strongly stretching the iris tissues.

Such a pupil expander can be installed in an eye with the pupil expanded at a moderate degree. However, in a case where the pupil is poorly expanded, it is very difficult to install the pupil expander in a small pupil, and therefore, the pupil must be largely expanded in an eccentric manner. Consequently, the pupil expander is likely to cause damage to the iris tissues.

Further, in a conventional pupil expander, such as, e.g., Malyugin Ring, to compensate for the disadvantage of returning to its original shape when inserted into an eye, it has been performed to hook the pupil expander on the pupillary margin while gradually releasing the pupil expander in a state in which the injector is inserted in the eye. However, it is difficult to hook the pupil expander on the pupillary margin of the iris, and it is not easy for everybody to do this. This is a very challenging task, particularly in the case of the pupil with a diameter smaller than 3 mm. Further, with regard to the removal, Malyugin Ring or the like is configured to be trapped into the injector within the eye, but there is a risk of causing damage to the iris during the operation.

The present invention has been made in view of the above-described problems. An object of the present invention is to provide a pupil expander capable of easily and safely expanding a pupil without causing damage to an intraocular tissue, such as, e.g., an iris, in ophthalmic surgery, such as, e.g., cataract surgery.

Means for Solving the Problems

According to the present invention, in order to attain the above-described object, a pupil expander used to expand a pupil in ophthalmic surgery is provided with:
a ring portion formed in a ring shape; and
an iris hooking portion provided to the ring portion,
wherein the ring portion includes a first ring portion formed in a shape curved radially inward and a second ring portion formed in a shape curved radially outward, the first ring portion and the second ring portion being arranged alternately along a circumferential direction of the ring portion,
wherein the first ring portion is provided with the iris hooking portion, and
wherein the iris hooking portion is configured to be hooked on a pupillary margin of an iris in a manner such that the first ring portion and the second ring portion are arranged on a front surface side of the iris.

With this configuration, at the time of hooking the iris hooking portions of one or a plurality of first ring portions on the pupillary margin of the iris, when an external force is applied to the first ring portion radially inward, the first ring portion is deformed to be further curved radially inward, and the second ring portions adjacent to the first ring portion are deformed while changing the curvature of the second ring portion radially outward. Therefore, the iris hooking portion of the first ring portion is greatly moved inward, while the radial movements of the iris hooking portions of first ring portions other than the first ring portion is suppressed. For this reason, in the case of performing ophthalmic surgery, such as, e.g., cataract surgery, the iris hooking portion of each first ring portion can be easily and assuredly hooked on the pupillary margin of the iris without causing damage to the intraocular tissues of the iris or the like by stretching greatly, thereby enabling easy and safe expansion of the pupil.

Further, it may be configured such that the ring portion is configured such that an amount of a radially outward movement of the iris hooking portion of the first ring portion other than the first ring portion to which an external force is applied is suppressed to 70% or less of an amount of a radially inward movement of the iris hooking portion of the first ring portion to which the external force is applied. With this configuration, it is possible to easily and securely hook the iris hooking portion of each first ring portion on a pupillary margin of an iris.

Further, it may be configured such that the second ring portion is formed of a material more easily elastically deformable in a radial direction than the first ring portion. With this configuration, the second ring portion is easily deformed while increasing the curvature in the radially outward direction. Therefore, it is possible to largely move the iris hooking portion of the first ring portion to which an external force is applied radially inward, and also possible to further suppress the movements of the iris hooking portions of the first ring portion to which an external force is not applied other than the first ring portion.

Further, it may be configured such that the second ring portion is formed, at its inner peripheral portion, with a groove extending in a thickness direction. With this configuration, the second ring portion is easily deformed while increasing the curvature radially outward. Therefore, it is possible to largely move the iris hooking portion of the first ring portion to which an external force is applied radially inward, and also possible to suppress the movement of the iris hooking portion of the first ring portion other than the first ring portion to which the external force is applied.

Further, it may be configured such that the iris hooking portion is formed in an L-shaped cross section composed of a hanging portion hanging from the first ring portion and an extension portion extending radially outward from the hanging portion, and is configured to be hooked on the pupillary margin of the iris in a manner such that the hanging portion is in contact with a side surface of the pupillary margin and the extension portion is in contact With a rear surface of the pupillary margin. With this configuration, the iris hooking portion of the first ring portion is fitted between the pupillary margin of the iris and the eyeball, and therefore, it is possible to hook the iris hooking portion on the pupillary margin of the iris.

Further, it may be configured such that the iris hooking portion extends radially outward in such a manner that the extension portion is inclined in either one of circumferential directions. With this configuration, when inserting the iris hooking portion between the pupillary margin of the iris and the eyeball, the inclined-side edge portion of the extension portion is easily hooked on the pupillary margin of the iris, which enables easy and assured hooking of the iris hooking portion on the pupillary margin of the iris. In addition, when removing the iris hooking portion from between the pupillary margin of the iris and the eyeball, the edge portion of the extension portion opposite to the inclination direction becomes less likely to be hooked on the pupillary margin of the iris. For this reason, it is possible to easily ad assuredly remove the iris hooking portion from the pupillary margin of the iris.

Further, it may be configured such that the first ring portion is provided with an instrument hook for hooking a medical instrument for ophthalmic surgery. With this configuration, by hooking a medical instrument for ophthalmic surgery on the instrument hook, an external force can be easily applied to the first ring portion radially inward.

It may be configured such that the first ring portion and/or the second ring portion is provided with an injector part hook for hooking a part of an injector for installing the pupil expander to the pupil or removing the pupil expander from the pupil. With this configuration, by hooking a component of an injector on the injector part hook, the pupil expander can be easily and assuredly installed on the pupil or removed from the pupil.

Further, it may be configured such that the first ring portion is inclined toward an iris side from a boundary connected to the second ring portion as it approaches a portion where the iris hooking portion is provided. With this configuration, since the iris hooking portion easily protrudes toward the rear surface of the iris due to the inclination of the first ring portion, the iris hooking portion can be easily and assuredly hooked on the pupillary margin of the iris.

It may be configured such that the second ring portion is inclined toward the iris side from a boundary connected to the first ring portion as it approaches a central portion. With this configuration, the central portion of the second ring portion assuredly comes into contact with the surface of the iris. Therefore, the pupillary margin of the iris becomes a state in which the pupillary margin of the iris is sandwiched between the second ring portion arranged on the front surface side of the iris and the iris hooking portion of the first ring portion arranged on the rear surface side of the iris, resulting in a stable installation of the pupil expander.

It may be configured such that the first ring portion is formed, at its inner peripheral portion or its outer peripheral portion, with a groove extending in a thickness direction. In particular, the groove is preferably formed on both sides of the iris hooking portion of the first ring portion. With this configuration, the first ring portion to which an external force is applied is easily deformed, which makes it possible to easily move the iris hooking portion of the first ring portion.

Effects of the Invention

According to the present invention, when an external force is applied to the first ring portion toward the radially inner side at the time of hooking the iris hooking portion of one or a plurality of first ring portions of the ring portion on the pupillary margin of the iris, the first ring portion is deformed to be further curved radially inward, and the second ring portions adjacent to the first ring portion are curved while increasing the curvature radially outward. Therefore, the iris hooking portion of the first ring portion is greatly moved radially inward, while the radial movements of the iris hooking portions of the first ring portions other than the first ring portion are suppressed. Therefore, in ophthalmic surgery, such as, e.g., cataract surgery, it is possible to easily and assuredly hook the iris hooking portion of each first ring portion on the pupillary margin of the iris without causing damage to intraocular tissues of the iris or the like by being largely expanded. Therefore, it is possible to easily and safely expand the pupil. Consequently, any surgeons can safely install the pupil expander in the pupil, which in turn can reduce the labor and the time in the surgery.

EMBODIMENTS FOR CARRYING OUT THE INVENTION

First Embodiment

Next, a first embodiment of a pupil expander according to the present invention will be described with reference to FIG. 1A to FIG. 8D.

[Configuration of Pupil Expander]

Figure 1A:
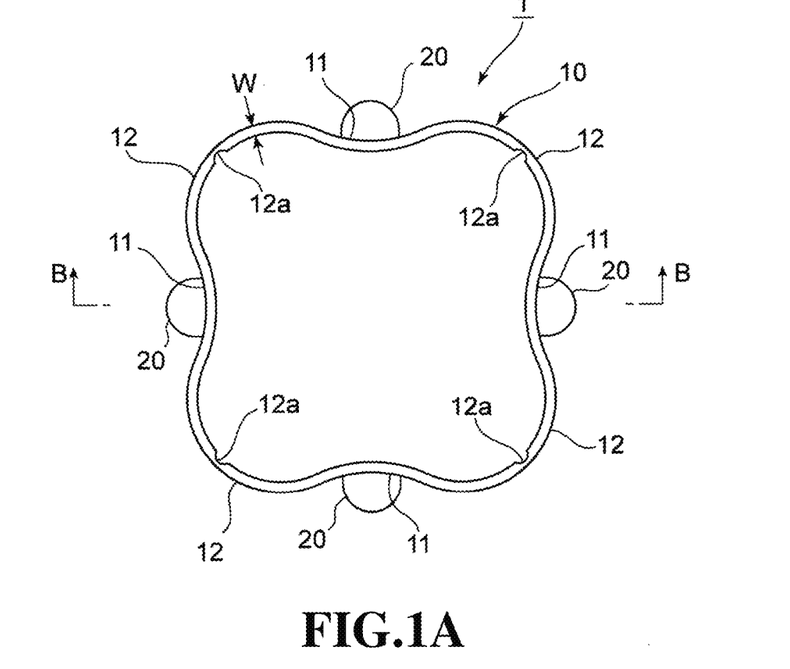
FIG. 1A is a plan view of a pupil expander according to a first embodiment of the present invention.
Figure 1B:
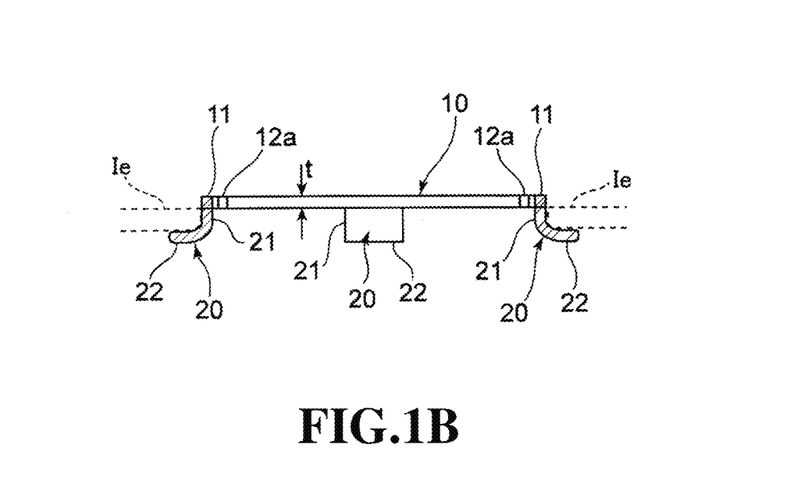
FIG. 1B is a cross-sectional view taken along the line B-B in FIG. 1A.

A pupil expander 1 according to this embodiment is used to expand a pupil P in ophthalmic surgery, such as, e.g., cataract surgery. As shown in FIG. 1A and FIG. 1B, the pupil expander 1 is provided with a ring portion 10 forming a ring and a plurality of iris hooking portions 20 provided to the ring portion 10. Note that in this specification, the term "radial direction" refers to the radial direction of the ring formed by the ring portion 10, and the term "circumferential direction" refers to the circumferential direction of the ring formed by the ring portion 10.

As shown in FIG. 1A and FIG. 1B, the ring portion 10 is formed of an elastically deformable member having a width "w" of 0.2 mm and a thickness "t" of 0.3 mm. The ring portion 10 is composed of four first ring portions 11 each curved radially inward along the circumferential direction and four second ring portions 12 each curved radially outward along the circumferential direction.

The first ring portions 11 and the second ring portions 12 are alternately arranged along the circumferential direction on the same plane and are connected to each other at the boundaries K to form a single ring. This ring portion 10 may be made of various materials. The ring portion 10 is preferably made of resin with high-shape-recovery properties or metal with high-shape-recovery properties. Examples of the resin with high-shape-recovery properties include polypropylene, polyester-based thermoplastic elastomer, olefin-based thermoplastic elastomer, urethane resin, acrylic resin, and silicone rubber. Examples of the metal with high-shape-recovery properties include titanium, nickel titanium, and stainless steel.

Figure 2:
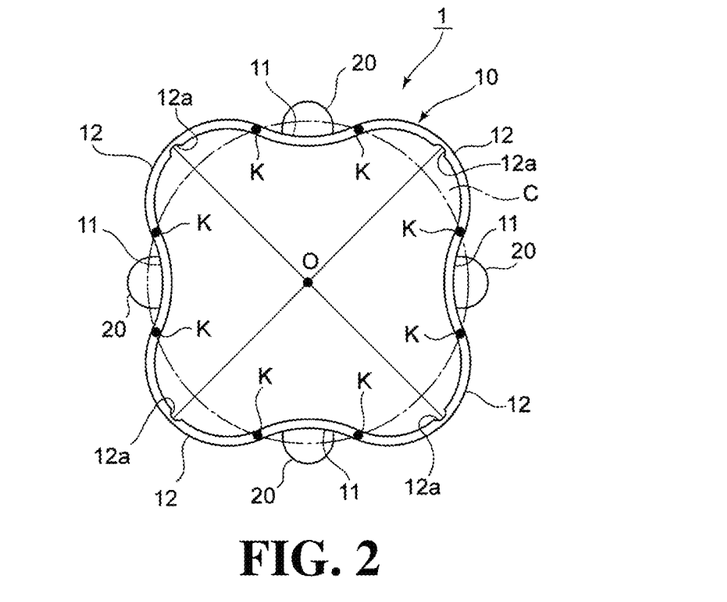
FIG. 2 is a plan view for explaining the shape of the pupil expander shown in FIGS. 1A and 1B.

As shown in FIG. 2, the first ring portion 11 is formed in such a manner as to curve radially inward between the boundaries K-K on both sides in the circumferential direction so as to depict a gentle substantially circular arc. The linear distance of the first ring portion 11 between the boundaries K-K is about 2.2 mm.

Further, the first ring portions 11 are arranged such that a pair of first ring portions 11 are arranged in a state of facing each other in the vertical direction in FIGS. 1A and 1B and the other pair of first ring portions 11 are arranged in a state of facing each other in the horizontal direction of FIGS. 1A and 1B.

The second ring portions 12 are formed in such a manner as to curve radially outward between the boundaries K-K on both sides in the circumferential direction to depict a gentle substantially circular arc. The linear distance of the second ring portion 12 between the boundaries K-K is about 3.3 mm.

Further, the second ring portions 12 are composed of a pair of second ring portions 12 arranged in a state of facing to each other in the oblique direction from the right obliquely upper side to the left obliquely lower side in FIGS. 1A and 1B and another pair of second ring portions 12 arranged in a state of facing to each other in the oblique direction from the left obliquely upper side to the right obliquely lower side in FIGS. 1A and 1B.

Further, the second ring portion 12 is formed, at its inner peripheral portion, with a groove 12a extending the thickness direction. With this configuration, as will be described later, the second ring portion 12 is easily deformed while increasing the curvature radially outward, which makes it possible to further suppress the movement of the iris hooking portion 20 of the first ring portion 11 (the first ring portion 11 other than the first ring portion 11 to which an external force is applied).

The relation between the first ring portion 11 and the second ring portion 12 will be described in detail. As shown in FIG. 2, an imaginary circle C passing through the respective boundaries K between the first ring portion 11 and the second ring portion 12 is assumed. In a natural state in which no external force is applied, the first ring portion 11 is formed in a state of being curved radially inward than the imaginary circle C. On the other hand, the second ring portion 12 is formed in a state of being curved radially outward than the imaginary circle C. Note that in this embodiment, as for the linear distance between the boundaries K-K of the first ring portion 11 and the second ring portion 12, the linear distance of the second ring portion 12 is formed to be larger than the linear distance of the first ring portion 11 in a natural state in which no external force is applied.

As shown in FIGS. 1A, 1B and FIG. 2, the iris hooking portion 20 is provided between the boundaries K-K on the outer peripheral surface of the first ring portion 11. As shown in FIG. 11B, this iris hooking portion 20 is formed into an L-shaped cross-section composed of a hanging portion 21 hanging from the rear surface of the first ring portion 11 and an extension portion 22 having a substantially semicircular shape in plan view extending radially outward from the hanging portion 21.

Thus, when the iris hooking portion 20 is hooked on the pupillary margin Ie of the iris I, the hanging portion 21 comes into contact with the side surface of the pupillary margin Ie of the iris I, and the extension portion 22 comes into contact with the rear surface of the pupillary margin Ie of the iris I. Thus, the iris hooking portion 20 of the first ring portion 11 is fitted between the pupillary margin Ie of the iris I and the eyeball. Therefore, the iris hooking portion 20 of the first ring portion 11 can be stably hooked on the pupillary margin Ie of the iris I.

[Basic Operation of Pupil Expander 1]

Next, the basic operation of this pupil expander 1 will be described with reference to FIG. 3 and FIG. 4.

Figure 3:
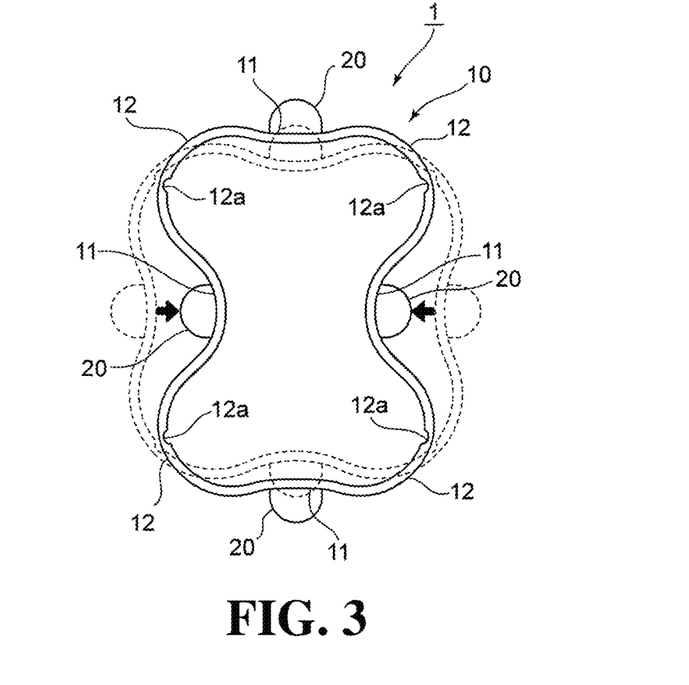
FIG. 3 is a plan view showing a state in which external forces are applied to the pupil expander shown in FIGS. 1A and 1B from both sides in the left-right direction toward the radially inner side.

FIG. 3 is a plan view showing the state in which an external force is applied to the pupil expander 1 radially inward from both sides in the left-right direction.

Specifically explaining, when the iris hooking portions 20 of the left and right first ring portions 11 of the pupil expander 1 are moved in the approaching direction, the left and right first ring portions 1I are deformed to be further curved radially inward. At this time, although the iris hooking portions 20 of the upper and lower first ring portions 11 move radially outward, the four second ring portions 12 adjacent to the left and right first ring portions 11 deform radially outward while largely increasing the curvature. Therefore, the movements of the iris hooking portions 20 of the upper and lower first ring portions 11 are suppressed.

Figure 4:
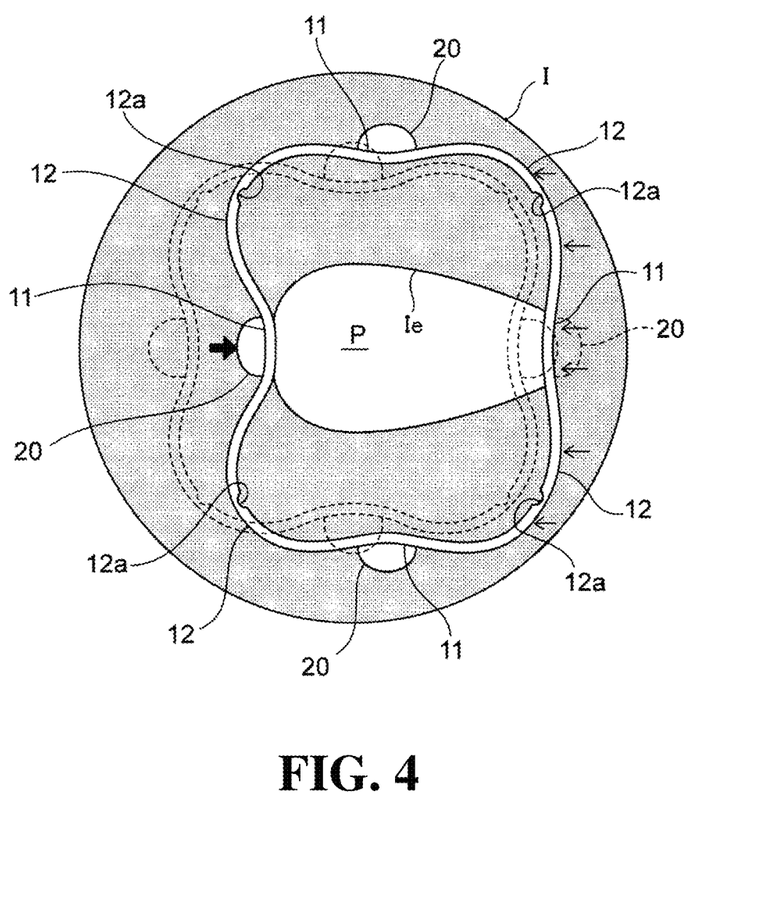
FIG. 4 is a plan view showing a state in which an external force is applied to the pupil expander shown in FIGS. 1A and 1B from the left direction toward the radially inner side.

FIG. 4 is a plan view showing the state in which an external force is applied to the pupil expander 1 radially inward from the left direction.

Specifically explaining, in a state in which the iris hooking portion 20 of the right side first ring portion 11 of the pupil expander 1 is hooked on the pupillary margin Ie of the iris I, the iris hooking portion 20 of the left side first ring portion 11 is moved in the direction to approach the iris hooking portion 20 of the right side first ring portion 11. As a result, the left first ring portion 11 is deformed to be further curved radially inward. At this time, the two second ring portions 12 adjacent to the left side first ring portion 11 are deformed while largely increasing the curvature radially outward, and therefore, the movements of the iris hooking portions 20 of the upper and lower first ring portions 11 are suppressed. Further, the iris hooking portion 20 of the right side first ring portion 11 is caused to be inclined by receiving a repulsive force from the pupillary margin Ie of the iris I, and therefore, the right side first ring portion 11 and the second ring portions 12 positioned on the both sides of the right side first ring portion 11 are caused to be inclined in the direction toward the rear of the right iris I. Therefore, the right side portion of the ring portion 10 receives the repulsive force from the iris I, thereby preventing the movement of the entire ring portion 10 toward the right side.

When an external force is applied radially inward to one or a plurality of first ring portions 11 as described above, the first ring portion 11 is deformed to be further curved radially inward, and the second ring portions 12 adjacent to both sides of the first ring portion 11 are deformed to increase the curvature. Therefore, the radially inward movements of the iris hooking portions 20 of the other first ring portions 11 are suppressed.

In particular, in this embodiment, the ring portion 10 is configured such that the radially outward movements of the iris hooking portions 20 of the first ring portions other than the first ring portion 11 to which the external force is applied are suppressed to 70% or less of the radially inward movement of the first ring portion 11 to which an external force is applied.

[Installation of Pupil Expander 1]

Next, the method of installing the pupil expander 1 to a pupil will be described with reference to FIG. 5A to FIG. 8D. Note that when installing the pupil expander 1 to a pupil, an incision (not shown) for inserting the pupil expander 1 through the cornea or an incision (not shown) for inserting a Sinskey hook 3 as a medical instrument (incision (not shown) for operating the pupil expander 1 is formed in the cornea in advance. For the convenience of explanation, the iris hooking portion 20 located on the right upper side, the iris hooking portion 20 located on the left upper side, the iris hooking portion 20 located on the left lower side, and the iris hooking portion 20 located on the lower right side in FIGS. 5A-5E, FIGS. 7A-7D, and FIGS. 8A-8D are respectively denoted by reference symbols of 20A, 20B, 20C, and 20D.

First, a process of installing the pupil expander 1 to a pupil P without using an injector will be described with reference to FIGS. 5A-5E.

Figure 5A:
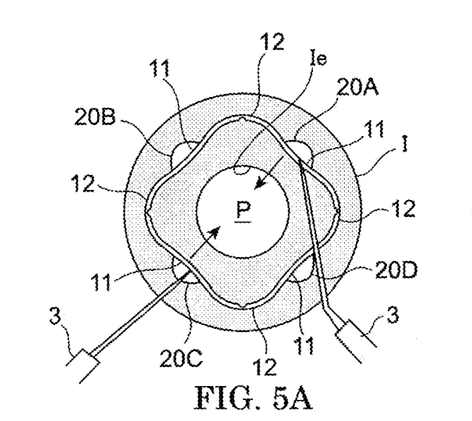
FIG. 5A is a plan view showing a first step of a process of installing the pupil expander shown in FIGS. 1A and 1B in the pupil without using an injector.
Figure 5B:
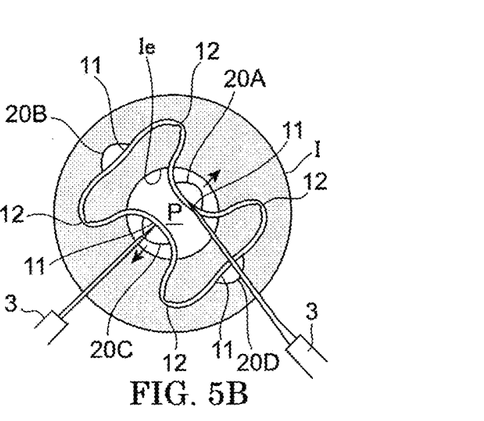
FIG. 5B is a plan view showing a second step of a process of installing the pupil expander shown in FIGS. 1A and 1B in the pupil without using an injector.

First, as shown in FIG. 5A, the pupil expander 1 is placed at a predetermined position on the front face of the iris I. Then, using Sinskey hooks 3, the iris hooking portions 20A and 20C of a first pair of first ring portions 11 (the right obliquely upper side first ring portion 11 and the left obliquely lower side first ring portion 11) are moved on the surface of the iris I in the direction of approaching to each other. With this, as shown in FIG. 5B, the first pair of first ring portions 11 are deformed to be further curved radially inward, so that the iris hooking portions 20A and 20C of the first pair of first ring portions 11 are hooked on the pupillary margin Ie of the iris I.

Figure 5C:
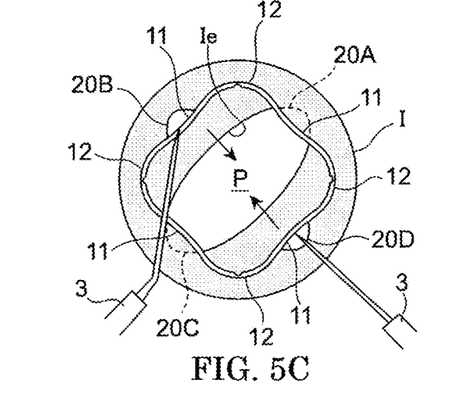
FIG. 5C is a plan view showing a third step of a process of installing the pupil expander shown in FIGS. 1A and 1B in the pupil without using an injector.

Next, as shown in FIG. 5C, when the Sinskey hooks 3 are removed from the iris hooking portions 20A and 20C of the first pair of first ring portions 11, the pupil expander 1 returns to its original state by its own elastic force. As a result, the iris hooking portions 20A and 20C of the first pair of first ring portions 11 move in the direction to separate from each other.

Figure 5D:
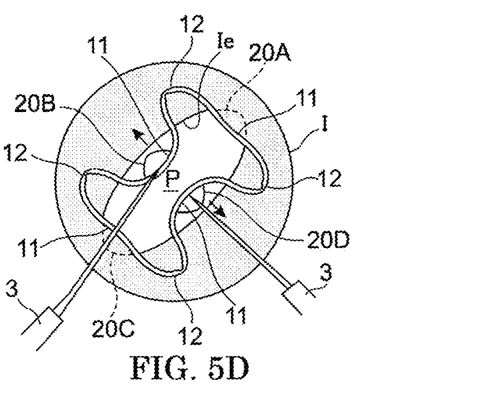
FIG. 5D is a plan view showing a fourth step of a process of installing the pupil expander shown in FIGS. 1A and 1B in the pupil without using an injector.

Next, as shown in FIG. 5D, the iris hooking portions 20B and 20D of a second pair of first ring portions 11 (the left obliquely upper side first ring portion 11 and the right obliquely lower side first ring portion 11) are moved in the direction to approach to each other with Sinskey hooks 3. With this, as shown in FIG. 5D, the second pair of first ring portions 11 are deformed to be further curved radially inward, and therefore, the iris hooking portions 20B and 20D of the second pair of first ring portions 11 are hooked on the pupillary margin Ie of the iris I. At this time, the iris hooking portions 20A and 20C of the first pair of first ring portions 11 (the right obliquely upper side first ring portion 11 and the left obliquely lower side first ring portion 11) attempt to move radially outward. However, the four second ring portions 12 adjacent to the second pair of first ring portions 11 are deformed while largely increasing the curvature radially outward, which suppresses the movements of the iris hooking portions 20A and 20C of the first pair of first ring portions 11.

Figure 5E:
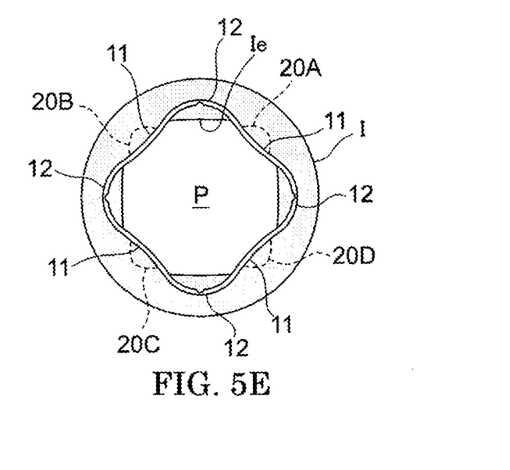
FIG. 5E is a plan view showing a fifth step of a process of installing the pupil expander shown in FIGS. 1A and 1B in the pupil without using an injector.

Finally, as shown in FIG. 5E, when the Sinskey hooks 3 are removed from the iris hooking portions 20B and 20D of the second pair of first ring portions 11, the pupil expander 1 returns to its original state by its own elastic force. As a result, the iris hooking portions 20A and 20C of the first pair of first ring portions 11 are slightly moved radially inward, and the iris hooking portions 20B and 20D of the second pair of first ring portions 11 are move radially outward.

Thus, as shown in FIG. 5E, in a state in which the ring portion 10 is arranged on the front side of the iris I, the iris hooking portions 20A to 20D of the first ring portion 11 are hooked on the pupillary margin Ie of the iris I. With this, it is possible to expanded the pupil P to an appropriate size.

Next, a process of installing the pupil expander 1 to a pupil P using an injector 2 will be described with reference to FIG. 6 to FIGS. 8A-8D.

Figure 6:
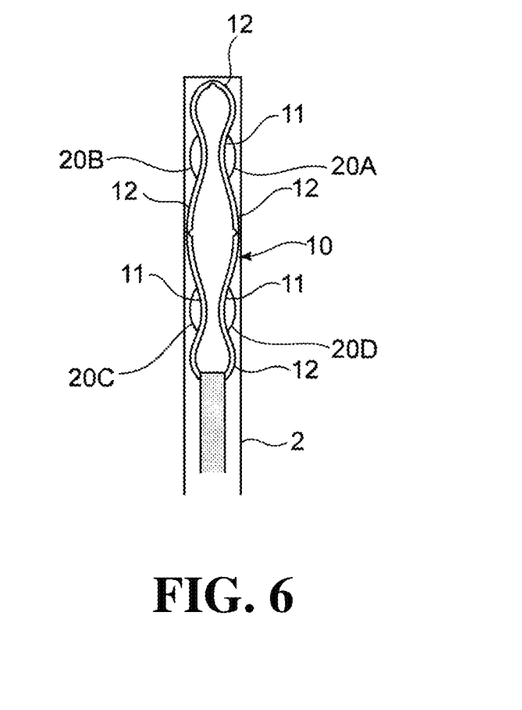
FIG. 6 is a diagram showing a state in which the pupil expander shown in FIGS. 1A and 1B is inserted in an injector.

First, as shown in FIG. 6, the pupil expander 1 is inserted into an injector 2. At this time, for the purpose of easily hooking the iris hooking portions 20 of the pupil expander 1 on the pupillary margin Ie of the iris I when pushing out the pupil expander 1 from the injector 2, the pupil expander 1 is inserted in the injector 2 in such a manner that the iris hooking portions 20A and 20B of the first ring portions 11 and the iris hooking portions 20C and 20D of the first ring portions 11 are aligned in parallel on the front side and the rear side, respectively.

Figure 7A:
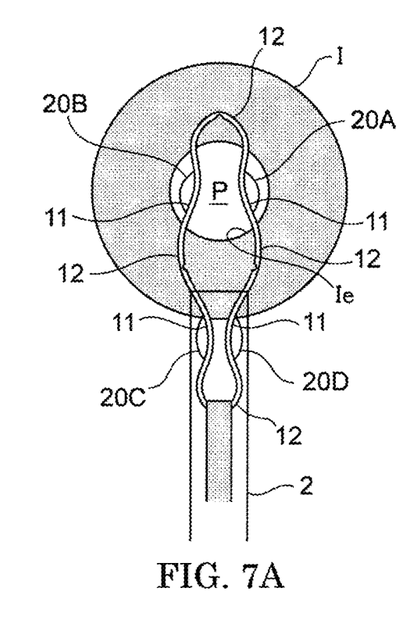
FIG. 7A is a plan view showing a first step of a process (first half) of installing the pupil expander shown in FIGS. 1A and 1B in the pupil using an injector.
Figure 7B:
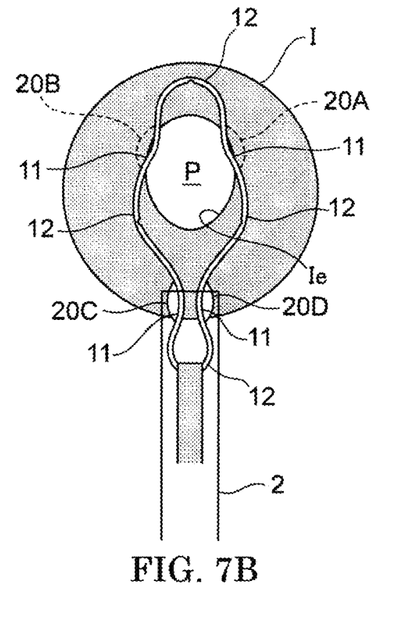
FIG. 7B is a plan view showing a second step of a process (first half) of installing the pupil expander shown in FIGS. 1A and 1B in the pupil using an injector.

Next, as shown in FIG. 7A, the pupil expander 1 is pushed out from the injector 2. Then, as shown in FIG. 7B, the iris hooking portions 20A and 20B of the iris I pupil expander 1 of the first pair of first ring portions 11 (the pair of first ring portions 11 on the upper side in FIGS. 7A-7D are caused to be hooked on the pupillary margin Ie of the iris I.

Figure 7C:
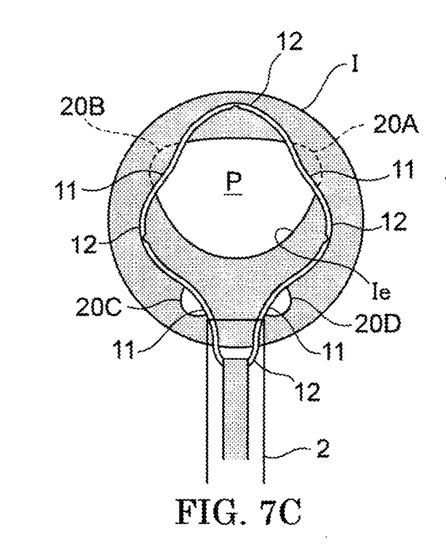
FIG. 7C is a plan view showing a third step of a process (first half) of installing the pupil expander shown in FIGS. 1A and 1B in the pupil using an injector.

Next, as shown in FIG. 7C, the pupil expander 1 is further pushed out from the injector 2. As a result, the pupil expander 1 returns to its original state by the elastic force of the ring portion 10. Therefore, the iris hooking portions 20A and 20B of the first pair of first ring portions 11 move in the direction to separate from each other.

Figure 7D:
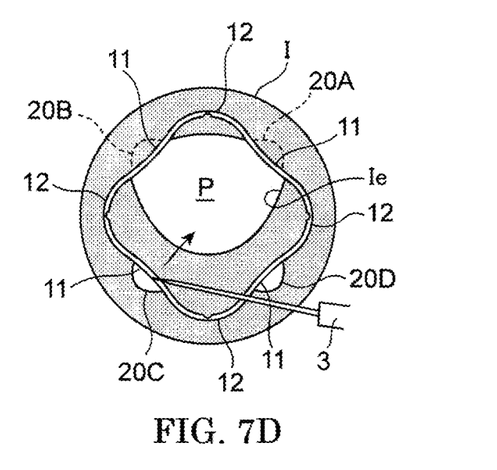
FIG. 7D is a plan view showing a fourth step of a process (first half) of installing the pupil expander shown in FIGS. 1A and 1B in the pupil using an injector.
Figure 8A:
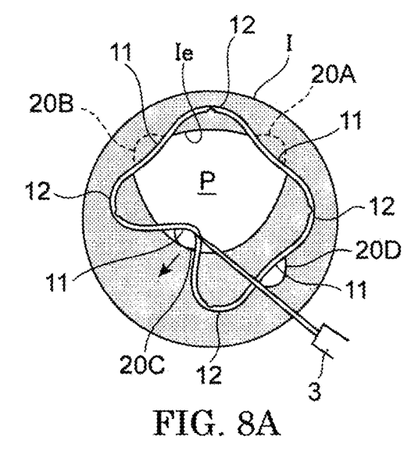
FIG. 8A is a plan view showing a first step of a process (second half) of installing the pupil expander shown in FIGS. 1A and 1B in the pupil using an injector.

Next, as shown in FIG. 7D, by completely pushing out the pupil expander 1 from the injector 2, the iris hooking portion 20C of the second first ring portion 11 (the first ring portion 11 on the left obliquely lower side in FIGS. 7A-7D is moved with a Sinskey hook 3 such that the iris hooking portion 20C of the first ring portion 11 (the first ring portion 11 on the left obliquely lower side in FIGS. 7A-7D is moved in the direction to approach the iris hooking portion 20A of the first ring portion 11 facing the surface of the iris I. With this, as shown in FIG. 8A, the second first ring portion 11 is deformed to be further curved radially inward, and therefore, the iris hooking portion 20C of the second first ring portion 11 is hooked on the pupillary margin Ie of the iris I as it is. At this time, the second ring portions 12 (the second ring portions 12 on the left side and the lower side in FIG. 8A) adjacent on both sides of the second first ring portion 11 are deformed while increasing the curvature radially outward. Therefore, the movements of the iris hooking portions 20B and 20D of the first ring portion 11 on the left obliquely upper side and the right obliquely lower side are suppressed. Further, the iris hooking portion 20A of the first ring portion 11 on the upper right obliquely side is inclined by receiving the repulsive forces from the pupillary margin Ie of the iris I. As a result, the first ring portion 11 on the right obliquely upper side and the second ring portion 12 on both sides thereof are inclined toward the rear of the iris I on the right obliquely upper side. Accordingly, the right obliquely upper side portion of the ring portion 10 receives the repulsive force from the iris I, and therefore, the movement of the entire ring portion 10 to the right obliquely upper side is suppressed.

Figure 8B:
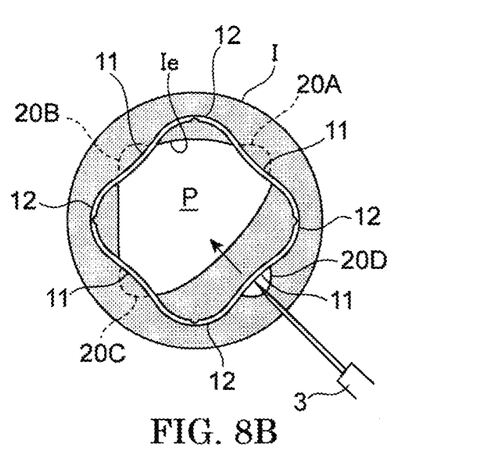
FIG. 8B is a plan view showing a second step of a process (second half) of installing the pupil expander shown in FIGS. 1A and 1B in the pupil using an injector.
Figure 8C:
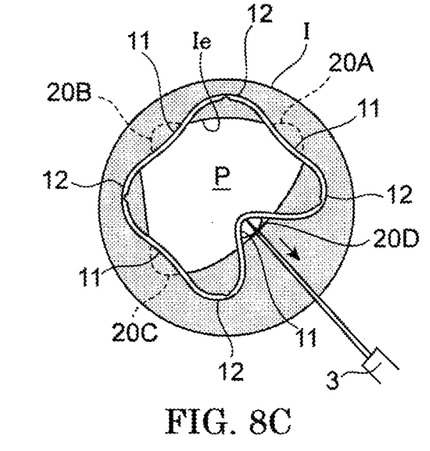
FIG. 8C is a plan view showing a third step of a process (second half) of installing the pupil expander shown in FIGS. 1A and 1B in the pupil using an injector.

Next, as shown in FIG. 8B, the iris hooking portion 20D of a third first ring portion 11 (the first ring portion 11 on the right obliquely lower side in FIGS. 8A-8D is moved with a Sinskey hook 3 in a direction to approach the iris hooking portion 20B of the first ring portion 11 facing the surface of the iris I. As a result, as shown in FIG. 8C, the third first ring portion 11 is deformed to be further curved radially inward, and therefore, the iris hooking portion 20D of the third first ring portion 11 is hooked on the pupillary margin Ie of the iris I. At this time, the second ring portions 12 (the second ring portion 12 on the right side and the second ring portion 12 on the lower side) adjacent on both sides of the third first ring portion 11 are deformed while increasing the curvature. Therefore, the movements of the iris hooking portions 20A and 20C of the first ring portions 11 on the right obliquely upper side and the left obliquely lower side are suppressed. Further, the iris hooking portion 20B of the first ring portion 11 on the left obliquely upper side is inclined by the repulsive force from the pupillary margin Ie of the iris I, and therefore, the first ring portion 10 on the left obliquely upper side and the second ring portions 12 on both sides of the first ring portion 10 are inclined rearward of the iris I on the left obliquely upper side. For this reason, the left obliquely upper side portion of the ring portion 10 receives the repulsive force from the iris I, and therefore, the movement of the entire ring portion 10 toward the left obliquely upper side is suppressed.

Figure 8D:
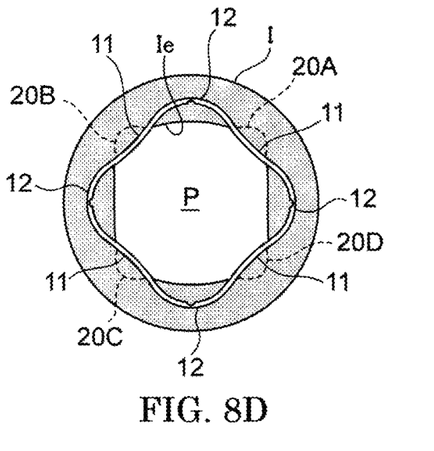
FIG. 8D is a plan view showing a fourth step of a process (second half) of installing the pupil expander shown in FIGS. 1A and 1B in the pupil using an injector.

Lastly, as shown in FIG. 8D, the Sinskey hook 3 is removed. With this, the pupil expander 1 returns to its original state by the elastic force of the ring portion 10. Thus, the iris hooking portions 20A to 20C of the first and second first ring portions 11 are moved slightly radially inward, and the third iris hooking portion 20D of the first ring portion 11 is moved radially outward.

Thus, as shown in FIG. 8D, in a state in which the ring portion 10 is arranged on the front face of the iris I, the iris hooking portions 20A to 20D of the first ring portions 11 are hooked on the pupillary margin Je of the iris L With this, it is possible to expand the pupil P to an appropriate size.

Figure 9:
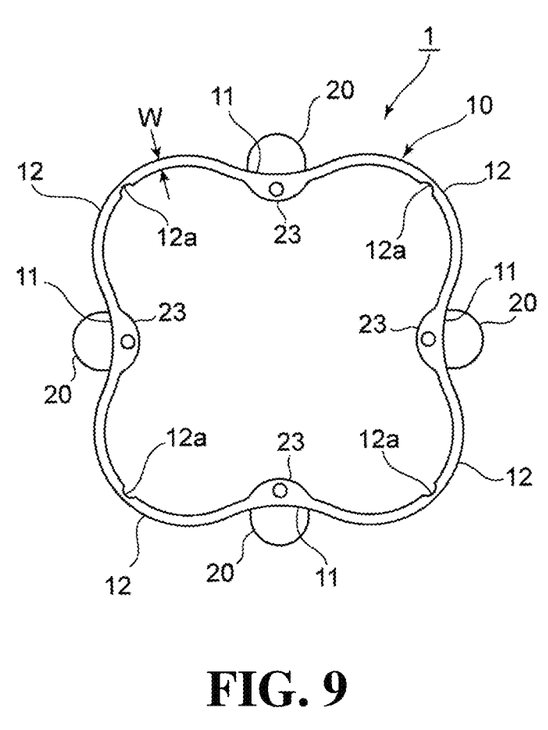
FIG. 9 is a plan view showing a pupil expander according to a modification of the first embodiment.

As shown in FIG. 9, the first ring portion 11 may be provided with an instrument hook 23 each for hooking a medical instrument for ophthalmic surgery.

The first ring portions 11 and/or the second ring portions 12 may be each provided with an injector part hook for hooking a part of an injector for installing or removing the pupil expander 1 to or from the pupil P.

Second Embodiment

Figure 10:
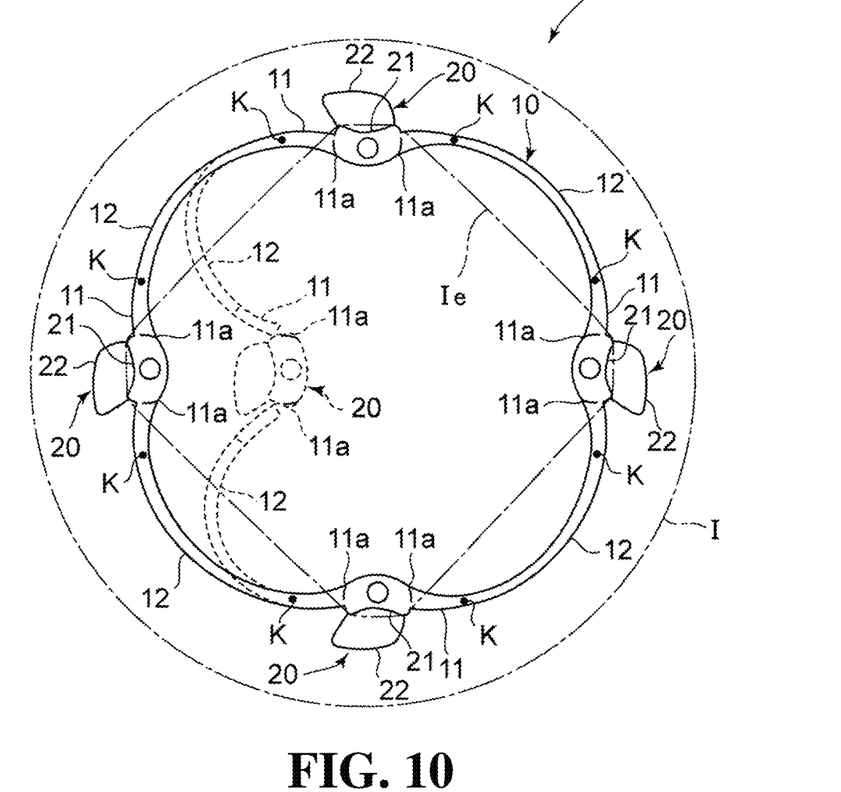
FIG. 10 is a plan view showing a pupil expander according to a second embodiment.

Next, a second embodiment of a pupil expander according to the present invention will be described with reference to FIG. 10 to FIG. 11. In the following description, only the configuration that differs from the embodiment described above will be described, and the description of the same configuration will be omitted, and the same reference symbol will be assigned. In FIG. 10, the state in which the first ring portion 11 is deformed to be moved radially inward is shown with dotted lines.

As shown in FIG. 10, the first ring portion 11 is formed, at its inner peripheral portion, with a groove 11a extending in the thickness direction. In this embodiment, the groove 11a is formed by being cut into a cutout shape in the thickness direction with a laser on both sides of the iris hooking portion 20 in the first ring portion 11.

According to this configuration, when the first ring portion 11 is deformed to be curved radially inward, the grooves 11a opens in the circumferential direction like a hinge, so that the iris hooking portion 20 of the first ring portion 11 can be easily moved radially inward. On the other hand, when the first ring portion 11 is deformed to return radially outward, the groove 11a closes like a hinge. As a result, the iris hooking portion 20 of the first ring portion 11 can be returned to a proper position on the radially outward side and can be stopped. In the first ring portion 11, from the viewpoint of ease of manufacturing, a groove 11a extending in the thickness direction may be formed at the outer peripheral portion.

Figure 11:
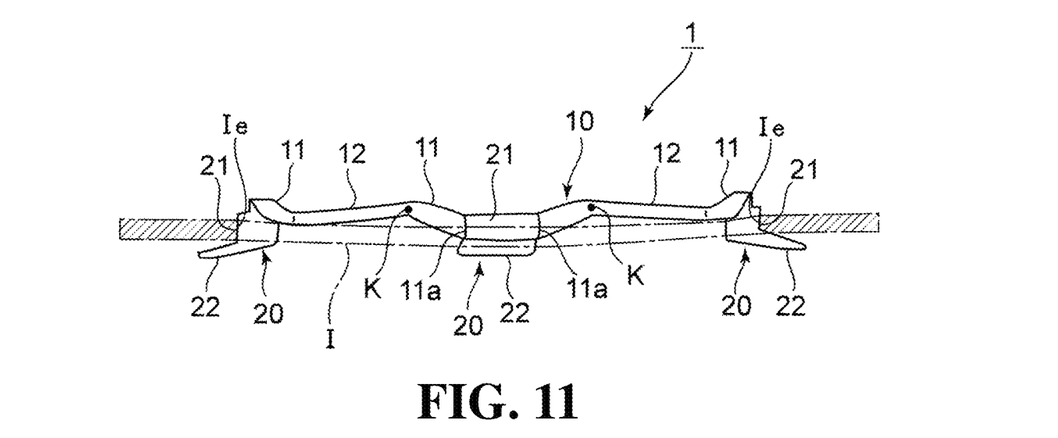
FIG. 11 is a side view of the pupil expander shown in FIG. 10.

Further, as shown in FIG. 11, the first ring portion 11 is inclined toward the iris I from the boundaries K connected to the second ring portions 12 as it approaches a part where the iris hooking portion 20 is provided. According to this configuration, the iris hooking portion 20 easily protrudes toward the rear surface of the iris I due to the inclination of the first ring portion 11. Therefore, it is possible to easily and assuredly hook the iris hooking portion 20 on the pupillary margin Ie of the iris I.

The second ring portion 12 is inclined toward the iris I from the boundaries K connected to the first ring portions 11 as it approaches the central portion. This ensures that the central portion of the second ring portion 12 assuredly comes into contact with the surface of the iris I. Therefore, the pupillary margin Ie of the iris I becomes a state to be sandwiched between the second ring portion 12 arranged on the front surface side of the iris I and the iris hooking portion 20 of the first ring portion 11 arranged on the rear surface side of the iris I, and therefore, the pupil expander 1 can be stably installed.

As shown in FIG. 10, the iris hooking portion 20 is formed in a parallelogram shape extending radially outward such that the extension portion 22 is inclined to either one of circumferential directions. According to this, when fitting the iris hooking portion 20 between the pupillary margin Ie of the iris I and the eyeball, the edge of the extension portion 22 on the inclination direction side is easily hooked on the pupillary margin Ie of the iris I. Therefore, it becomes possible to easily and assuredly hook the iris hooking portion 20 on the pupillary margin Ie of the iris I. Further, when removing the iris hooking portion 20 from between the pupillary margin Ie of the iris I and the eyeball, the edge of the extension portion 22 on the edge side opposite to the inclination direction is less likely to be hooked by the pupillary margin Ie of the iris L Therefore, it becomes possible to easily and assuredly remove the iris hooking portion 20 from the pupillary margin Ie of the iris I.

The embodiments of the present invention have been described above with reference to the attached drawings, but the present invention is not limited to the illustrated embodiments. It should be understood that various modifications and variations can be made to the illustrated embodiments falling within the same as or equivalent to the scope of the present invention.

DESCRIPTION OF SYMBOLS

1: Pupil expander
10: Ring portion

11: First ring portion
12: Second ring portion
20: Iris hooking portion
21: Hanging portion
22: Extension portion
2: Injector

The invention claimed is:

1. A pupil expander used to expand a pupil in ophthalmic surgery, comprising:
a ring portion formed in a ring shape; and
iris hooking portions provided to the ring portion,
wherein the ring portion includes first ring portions and second ring portions that are arranged alternately along a circumferential direction of the ring portion,
wherein each of the first ring portions is formed in a shape curved radially inward and each of the second ring portions is formed in a shape curved radially outward so that each of the first ring portions and the second ring portions is in an arc-shape,
wherein the first ring portions are individually provided with an iris hooking portion of the iris hooking portions,
wherein the iris hooking portions are configured to be hooked on a pupillary margin of an iris in a manner such that the first ring portions and the second ring portions are arranged on a front surface side of the iris, and
wherein the ring portion is configured such that an amount of radially outward movement of the iris hooking portions of the first ring portions other than the first ring portions to which an external force is applied is suppressed to 70% or less of an amount of a radially inward movement of the iris hooking portions of the first ring portions to which the external force is applied.

2. The pupil expander as recited in claim 1,
wherein the second ring portions are formed of a material more easily elastically deformable in a radial direction than the first ring portions.

3. The pupil expander as recited in claim 1,
wherein each of the second ring portions is formed, at its inner peripheral portion, with a groove extending in a thickness direction.

4. The pupil expander as recited in claim 1,
wherein each of the first ring portions is configured to incline toward an iris side from a boundary connected to an adjacent second ring portion as it approaches a portion where an iris hooking portion among the iris hooking portions is provided.

5. The pupil expander as recited in claim 4,
wherein each of the second ring portions is configured to incline toward the iris side from a boundary connected to an adjacent first ring portion as it approaches a central portion.

6. The pupil expander as recited in claim 1,
wherein each of the first ring portions is formed, at its inner peripheral portion or its outer peripheral portion, with a groove extending in a thickness direction.

7. The pupil expander as recited in claim 1,
wherein the first ring portions and the second ring portions are connected to each other at boundaries to form a single ring.

8. A pupil expander used to expand a pupil in ophthalmic surgery, comprising:
a ring portion formed in a ring shape; and
iris hooking portions provided to the ring portion,
wherein the ring portion includes first ring portions and second ring portions that are arranged alternately along a circumferential direction of the ring portion,
wherein each of the first ring portions is formed in a shape curved radially inward and each of the second ring portions is formed in a shape curved radially outward so that each of the first ring portions and the second ring portions is in an arc-shape,
wherein the first ring portions are individually provided with an iris hooking portion of the iris hooking portions,
wherein the iris hooking portions are configured to be hooked on a pupillary margin of an iris in a manner such that the first ring portions and the second ring portions are arranged on a front surface side of the iris, and
wherein each of the iris hooking portions is formed in an L-shaped cross section composed of a hanging portion hanging from the first ring portions and an extension portion extending radially outward from the hanging portion, and is configured to be hooked on the pupillary margin of the iris in a manner such that the hanging portion is in contact with a side surface of the pupillary margin and the extension portion is in contact with a rear surface of the pupillary margin.

9. The pupil expander as recited in claim 2,
wherein each of the iris hooking portions extends radially outward in such a manner that the extension portion is inclined in either one of circumferential directions.

10. A pupil expander used to expand a pupil in ophthalmic surgery, comprising:
a ring portion formed in a ring shape; and
iris hooking portions provided to the ring portion,
wherein the ring portion includes first ring portions and second ring portions that are arranged alternately along a circumferential direction of the ring portion,
wherein each of the first ring portions is formed in a shape curved radially inward and each of the second ring portions is formed in a shape curve radially outward so that each of the first ring portions and the second ring portions is in an arc-shape,
wherein the first ring portions are individually provided with an iris hooking portion of the iris hooking portions,
wherein the iris hooking portions are configured to be hooked on a pupillary margin of an iris in a manner such that the first ring portions and the second ring portions are arranged on a front surface side of the iris, and
wherein each of the first ring portions is provided with an instrument hook for hooking a medical instrument for ophthalmic surgery.

11. A pupil expander used to expand a pupil in ophthalmic surgery, comprising:
a ring portion formed in a ring shape; and
iris hooking portions provided to the ring portion,
wherein the ring portion includes first ring portions and second ring portions that are arranged alternately along a circumferential direction of the ring portion,
wherein each of the first ring portions is formed in a shape curved radially inward and each of the second ring portions is formed in a shape curved radially outward so that each of the first ring portions and the second ring portions is in an arc-shape,
wherein the first ring portions are individually provided with an iris hooking portion of the iris hooking portions, wherein the iris hooking portions are configured to be hooked on a pupillary margin of an iris in a manner such that the first ring portions and the second ring portions are arranged on a front surface side of the iris, wherein the first ring portions and the second ring portions are connected to each other at boundaries to form a single ring, wherein the boundaries are arranged in a manner that an imaginary circle passing through the boundaries is formed, and wherein each of the first ring portions is curved radially inward with respect to the imaginary circle, and each of the second ring portions is curved radially outward with respect to the imaginary circle.

* * * * *